United States Patent
Rose et al.

(10) Patent No.: US 9,150,623 B2
(45) Date of Patent: Oct. 6, 2015

(54) DELAYED FRUIT DETERIORATION ALLELE IN PLANTS AND METHODS OF DETECTION

(75) Inventors: Jocelyn Kenneth Rose, Ithaca, NY (US); Tal Isaacson-Lustig, Arava (IL); Julia Vrebalov, Ithaca, NY (US)

(73) Assignees: Cornell Research Foundation, Inc., Ithaca, NY (US); Boyce Thompson Institute for Plant Research, Ithaca, NY (US)

( * ) Notice: Subject to any disclaimer, the term of this patent is extended or adjusted under 35 U.S.C. 154(b) by 1064 days.

(21) Appl. No.: 12/993,229

(22) PCT Filed: May 19, 2009

(86) PCT No.: PCT/US2009/044522
§ 371 (c)(1),
(2), (4) Date: Feb. 1, 2012

(87) PCT Pub. No.: WO2009/143155
PCT Pub. Date: Nov. 26, 2009

(65) Prior Publication Data
US 2012/0054907 A1    Mar. 1, 2012

Related U.S. Application Data

(60) Provisional application No. 61/054,386, filed on May 19, 2008.

(51) Int. Cl.
| | |
|---|---|
| *A01H 5/08* | (2006.01) |
| *C07K 14/415* | (2006.01) |
| *C12N 15/82* | (2006.01) |
| *C12Q 1/68* | (2006.01) |

(52) U.S. Cl.
CPC .......... *C07K 14/415* (2013.01); *C12N 15/8262* (2013.01); *C12N 15/8266* (2013.01); *C12Q 1/6895* (2013.01)

(58) Field of Classification Search
USPC ........................................................ 800/290
See application file for complete search history.

(56) References Cited

U.S. PATENT DOCUMENTS

| | | | |
|---|---|---|---|
| 6,762,347 B1 * | 7/2004 | Giovannoni et al. | ......... 800/286 |
| 2005/0076410 A1 | 4/2005 | Giovannoni et al. | |

FOREIGN PATENT DOCUMENTS

WO     2007/112430 A2     10/2007

OTHER PUBLICATIONS

UniProtKB Accession No. Q56UP7 ([online], [retrieved on Mar. 14, 2013], retrieved from the internet < http://www.uniprot.org/uniprot/Q56UP7>).*
(Rose et al., Characterization of DFD (Delayed Fruit Deterioration): a New Tomato Mutant, 682 ISHS Acta Hort., Proc. 5th Postharvest Symp., 79-84 at 80 (2005)).*
Saladie et al. "A Reevaluation of the Key Factors that Influence Tomato Fruit Softening and Integrity", Plant Physiology 144:1012-1028 (2007).
Malyshev et al. "Solanium Lycopersicum Mutant NAC Domain Protein (NAC-NOR) Gene, NAC-NOR-alc Allele, Complete Cds" www.ncbi.nlm.nih.gov/nuccore/211996989 (2008).
Rose et al. "Use of the Tomato Delayed Fruit Deterioration (DFD) Mutant to Characterize and Enhance Fruit Quality Traits" www.reeis.usda.gov/web/crisprojectpages/205387 (2008).
PCT International Search Report for PCT/US2009/044522, filed May 19, 2009, completed Oct. 8, 2009.
PCT International Written Opinion for PCT/US2009/044522, filed May 19, 2009, mailed Feb. 26, 2010.

* cited by examiner

*Primary Examiner* — Medina A Ibrahim
(74) *Attorney, Agent, or Firm* — LeClairRyan, a Professional Corporation

(57) ABSTRACT

Disclosed is an isolated nucleic acid molecule comprising a nucleotide sequence that is at least 90% identical to a nucleotide sequence encoding a protein having the amino acid sequence of SEQ ID NO 4, wherein the protein has an aspartic acid (Asp) at amino acid position 106 Transgenic plants comprising the nucleic acid have reduced or delayed softening and detenoration of fruit compared to wild-type plants Methods of genetic screening for plants having reduced or delayed softening and detenoration of fruit, isolated oligonucleotides, and a method of imparting to a plant the dfd trait are also disclosed.

6 Claims, 1 Drawing Sheet

Extent of Wrinkling

SEQUENCE LISTING

<160> NUMBER OF SEQ ID NOS: 13

<210> SEQ ID NO 1
<211> LENGTH: 355
<212> TYPE: PRT
<213> ORGANISM: Solanum lycopersicum

<400> SEQUENCE: 1

```
Met Glu Ser Thr Asp Ser Ser Thr Gly Thr Arg His Gln Pro Gln Leu
1               5                   10                  15

Pro Pro Gly Phe Arg Phe His Pro Thr Asp Glu Glu Leu Ile Val His
            20                  25                  30

Tyr Leu Lys Lys Arg Val Ala Gly Ala Pro Ile Pro Val Asp Ile Ile
        35                  40                  45

Gly Glu Ile Asp Leu Tyr Lys Phe Asp Pro Trp Glu Leu Pro Ala Lys
    50                  55                  60

Ala Ile Phe Gly Glu Gln Glu Trp Phe Phe Ser Pro Arg Asp Arg
65                  70                  75                  80

Lys Tyr Pro Asn Gly Ala Arg Pro Asn Arg Ala Ala Thr Ser Gly Tyr
                85                  90                  95

Trp Lys Ala Thr Gly Thr Asp Lys Pro Val Phe Thr Ser Gly Gly Thr
            100                 105                 110

Gln Lys Val Gly Val Lys Lys Ala Leu Val Phe Tyr Gly Gly Lys Pro
        115                 120                 125

Pro Lys Gly Val Lys Thr Asn Trp Ile Met His Glu Tyr Arg Val Val
    130                 135                 140

Glu Asn Lys Thr Asn Asn Lys Pro Leu Gly Cys Asp Asn Ile Val Ala
145                 150                 155                 160

Asn Lys Lys Gly Ser Leu Arg Leu Asp Asp Trp Val Leu Cys Arg Ile
                165                 170                 175

Tyr Lys Lys Asn Asn Thr Gln Arg Ser Ile Asp Asp Leu His Asp Met
            180                 185                 190

Leu Gly Ser Ile Pro Gln Asn Val Pro Asn Ser Ile Leu Gln Gly Ile
        195                 200                 205

Lys Pro Ser Asn Tyr Gly Thr Ile Leu Leu Glu Asn Glu Ser Asn Met
    210                 215                 220

Tyr Asp Gly Ile Met Asn Thr Asn Asp Ile Ile Asn Asn Asn Asn
225                 230                 235                 240

Arg Ser Ile Pro Gln Ile Ser Ser Lys Arg Thr Met His Gly Gly Leu
                245                 250                 255

Tyr Trp Asn Asn Asp Glu Ala Thr Thr Thr Thr Thr Ile Asp Arg
            260                 265                 270

Asn His Ser Pro Asn Thr Lys Arg Phe Leu Val Glu Asn Glu Asp
        275                 280                 285

Asp Gly Leu Asn Met Asn Asn Ile Ser Arg Ile Thr Asn His Glu Gln
    290                 295                 300

Ser Ser Ser Ile Ala Asn Phe Leu Ser Gln Phe Pro Gln Asn Pro Ser
305                 310                 315                 320

Ile Gln Gln Gln Gln Gln Gln Glu Glu Val Leu Gly Ser Leu Asn
                325                 330                 335

Asp Gly Val Val Phe Arg Gln Pro Tyr Asn Gln Val Thr Gly Met Asn
            340                 345                 350

Trp Tyr Ser
        355
```

```
<210> SEQ ID NO 2
<211> LENGTH: 1423
<212> TYPE: DNA
<213> ORGANISM: Solanum lycopersicum

<400> SEQUENCE: 2
ctaaattcct tcttgtttat cattttctct cttcccaaaa aaaaaatccc aaaatttaat      60
cataatacaa ttcgaattta tcaacctcgt actacgtaca tattttttgtt ggtacgtaaa     120 atactgaatt caggtcaact caaacatcgt aaattgtgat ttctttatgg aaagtacgga     180
ttcatcaacc gggacacgtc atcagcctca actcccaccg gggtttcgat tccacccgac     240
ggacgaagaa ctcatcgtcc actacctcaa aaaacgagtc gccggcgctc cgattccggt     300
ggatattatt ggtgaaattg atctttataa gtttgatcca tgggaactcc ctgctaaggc     360
aatattcgga gagcaagaat ggttcttttt tagtccaaga gatagaaaat atcctaacgg     420
ggcgaggcca aatcgggctg caacatcggg ttattggaag gctaccggaa ccgacaagcc     480 ggttttttact tccggtggaa cacaaaaggt tgggtaaaa aaggcgctcg tttttttacgg     540 cggtaaacca ccaaaagggg taaaaactaa ttggatcatg catgaataca gagttgtaga     600
aaataaaaca aataacaagc cacttggttg tgataatatt gttgccaaca aaaaaggatc     660
tttgaggcta gatgattggg ttttatgtcg aatttacaag aagaataaca cacaaaggtc     720
catagatgat ttgcatgata tgttgggatc gataccacaa aatgtaccaa attcaatatt     780
acaaggaata aagccttcaa actatggtac aatattgctc gaaaatgaat cgaatatgta     840
cgatggaatt atgaataaca cgaacgatat tatcaacaat aataatagat ccattccaca     900
aatatcgtca aagagaacga tgcatggagg tttgtattgg aataacgacg aagcaacaac     960
aacaacaaca actattgata ggaaccattc tccaaataca aaaaggttcc ttgttgagaa    1020
caacgaggac gatggactta acatgaataa tatttcgcga attacaaatc atgaacaaag    1080
tagctccatt gccaatttcc tgagccagtt tcctcaaaat ccttcgattc aacaacaaca    1140
acaacaacaa gaagaagtat tgggatctct taatgatggg gtcgtctttc gacaacctta    1200
taatcaagtt actggcatga attggtactc ttaaagatat aaaaaggcaa aaaatagtta    1260
gccctgtaaa atcaatcgat caatcaatca tagatatatt atatatggat ttcgttatat    1320
tttactttta gttagaatta atatatagaa tatcttctat ctcacattaa caaataagaa    1380
catttataac aaaaaaaaaa aaaaaaaaaa aaaaaaaaaa aaa                       1423

<210> SEQ ID NO 3
<211> LENGTH: 2885
<212> TYPE: DNA
<213> ORGANISM: Solanum lycopersicum

<400> SEQUENCE: 3
ctaaattcct tcttgtttat cattttctct cttcccaaaa aaaatccca aatttaatc       60 ataatacaat tcgaattat caacctcgta ctacgtacat atttttgttg gtacgtaaaa     120
tactgaattc aggtcaactc aaacatcgta aattgtgatt tctttatgga agtacggat     180 tcatcaaccg ggacacgtca tcagcctcaa ctcccaccgg ggtttcgatt ccacccgacg    240
gacgaagaac tcatcgtcca ctacctcaaa aaacgagtcg ccggcgctcc gattccggtg    300
gatattattg gtgaaattga tctttataag tttgatccat gggaactccc tggtactatt    360
ttcaccacta tactatattt tcttgcccta taacttatat ataggggaaa aagatcggag    420
tcagcgatga acaattattg tgtctaaatt aaattttaaa tatgcaatag attggtgacg    480
```

```
aatttcgttg ctaattaatt ttttagtgat aaattaatat ttttcccctt tttaatcttc      540 atgttttta tcacaaagtt ttctatgacc aacttataaa gatttgaact cgatcaattt       600
tttttttaga atgaatgaac ttatgttata tatagtgata ttttaaatgc ttttttatat      660
tttcaaaaga tatccacgat aacgtgtaaa aagtgaattt gcaaaaaaaa aaatgtagta      720 cctttttattt aatttttattg tagataattt agattttaat tttgaatttg tttaatttaa   780
attctgaatc gtataatatt tatttaattt ctatttttg agttttttt tggagggtgc       840 ttaaaaagta gtattcacaa atataaagta gtggacaaac ataaagtagt ggacccataa     900
tttatttttt taaaaattat attaaaacta tttgttaagt ttaaattctg aattatcttc     960
ttatcatgtg tttaacgcag ctaaggcaat attcggagag caagaatggt tctttttag    1020 tccaagagat agaaaatatc ctaacggggc gaggccaaat cgggctgcaa catcgggtta   1080
ttggaaggct accggaaccg acaagccggt ttttacttcc ggtggaacac aaaaggttgg   1140
ggtaaaaaag gcgctcgttt tttacggcgg taaaccacca aaggggtaa aaactaattg    1200 gatcatgcat gaatacagag ttgtagaaaa taaaacaaat aacaagccac ttggttgtga   1260
taatattgtt gccaacaaaa aaggatcttt gagggtaagt cctaaatttt gcatcgaaac   1320
taatttctct atcgtatcag atagggataa gatatacgta tactctaatc tccttgaacc   1380
ccacaagtac tatactagat atgttgttgt tgtagatgac ttgattcaac tttcaaattt   1440
ttgatgaaaa tgtttaagtt atatatacat atatatatag gcggagctaa aaatttcgat   1500 aaggggggttt aaatctgaaa aaatggatat acgaaatagc cgaagaggt tcgacataga   1560 ttatttaac catataaaaa taatacaatt ttcatatata tatacgcgtg gttaatatga    1620
ggaatatttt atactattaa tgtactttaa ccaggggcgg ctctagagtt gatgaaccct   1680
ctcagcgaaa atttacgttg tatatttaag gtaccttta ataattttg tatttatata    1740 ttaatttga acctcttgaa tataagatta gacgttgact tagtggttc aggggttcaa     1800 atcactattc ttttttttcct aaccccctta atgaaaatcc tgaatcggcc actaacttta  1860
actggttata gaaggttaat cttactagaa aaaagcatga aattctaacc gacaaagatg   1920
tagtcgccca gttagataag acgtttaaat tgggacggat agagttactt tattttttcac  1980 tgtcatatgt tactatatat tgacacttca cttaaagagt tatcatatcg atatttttac  2040
tattagtgta cataacacaa actcgaataa attcaatgtt tcattagcta gttaattagt   2100 ctaactttttt taaaaaaaaa tattttttctt actccacact attttatttt attttttttgc 2160 agctagatga ttgggtttta tgtcgaattt acaagaagaa taacacacaa aggtccatag   2220
atgatttgca tgatatgttg ggatcgatac cacaaaatgt accaaattca atattacaag   2280
gaataaagcc ttcaaactat ggtacaatat tgctcgaaaa tgaatcgaat atgtacgatg   2340
gaattatgaa taacacgaac gatattatca acaataataa tagatccatt ccacaaatat   2400
cgtcaaagag aacgatgcat ggaggtttgt attggaataa cgacgaagca acaacaacaa   2460
caacaactat tgataggaac cattctccaa atacaaaaag gttccttgtt gagaacaacg   2520
aggacgatgg acttaacatg aataatattt cgcgaattac aaatcatgaa caaagtagct   2580
ccattgccaa tttcctgagc cagtttcctc aaaatccttc gattcaacaa caacaacaac   2640
aacaagaaga agtattggga tctcttaatg atggggtcgt ctttcgacaa ccttataatc   2700
aagttactgg catgaattgg tactcttaaa gatataaaaa ggcaaaaaat agttagccct   2760
gtaaaatcaa tcgatcaatc aatcatagat atattatata tggatttcgt tatattttac   2820
```

```
ttttagttag aattaatata tagaatatct tctatctcac attaacaaat aagaacattt    2880
ataac                                                                2885
```

<210> SEQ ID NO 4
<211> LENGTH: 355
<212> TYPE: PRT
<213> ORGANISM: Solanum lycopersicum

<400> SEQUENCE: 4

```
Met Glu Ser Thr Asp Ser Ser Thr Gly Thr Arg His Gln Pro Gln Leu
1               5                   10                  15

Pro Pro Gly Phe Arg Phe His Pro Thr Asp Glu Glu Leu Ile Val His
            20                  25                  30

Tyr Leu Lys Lys Arg Val Ala Gly Ala Pro Ile Pro Val Asp Ile Ile
        35                  40                  45

Gly Glu Ile Asp Leu Tyr Lys Phe Asp Pro Trp Glu Leu Pro Ala Lys
    50                  55                  60

Ala Ile Phe Gly Glu Gln Glu Trp Phe Phe Phe Ser Pro Arg Asp Arg
65                  70                  75                  80

Lys Tyr Pro Asn Gly Ala Arg Pro Asn Arg Ala Ala Thr Ser Gly Tyr
                85                  90                  95

Trp Lys Ala Thr Gly Thr Asp Lys Pro Asp Phe Thr Ser Gly Gly Thr
            100                 105                 110

Gln Lys Val Gly Val Lys Lys Ala Leu Val Phe Tyr Gly Gly Lys Pro
        115                 120                 125

Pro Lys Gly Val Lys Thr Asn Trp Ile Met His Glu Tyr Arg Val Val
    130                 135                 140

Glu Asn Lys Thr Asn Asn Lys Pro Leu Gly Cys Asp Asn Ile Val Ala
145                 150                 155                 160

Asn Lys Lys Gly Ser Leu Arg Leu Asp Asp Trp Val Leu Cys Arg Ile
                165                 170                 175

Tyr Lys Lys Asn Asn Thr Gln Arg Ser Ile Asp Asp Leu His Asp Met
            180                 185                 190

Leu Gly Ser Ile Pro Gln Asn Val Pro Asn Ser Ile Leu Gln Gly Ile
        195                 200                 205

Lys Pro Ser Asn Tyr Gly Thr Ile Leu Leu Glu Asn Glu Ser Asn Met
    210                 215                 220

Tyr Asp Gly Ile Met Asn Asn Thr Asn Asp Ile Ile Asn Asn Asn Asn
225                 230                 235                 240

Arg Ser Ile Pro Gln Ile Ser Ser Lys Arg Thr Met His Gly Gly Leu
                245                 250                 255

Tyr Trp Asn Asn Asp Glu Ala Thr Thr Thr Thr Thr Thr Ile Asp Arg
            260                 265                 270

Asn His Ser Pro Asn Thr Lys Arg Phe Leu Val Glu Asn Asn Glu Asp
        275                 280                 285

Asp Gly Leu Asn Met Asn Asn Ile Ser Arg Ile Thr Asn His Glu Gln
    290                 295                 300

Ser Ser Ser Ile Ala Asn Phe Leu Ser Gln Phe Pro Gln Asn Pro Ser
305                 310                 315                 320

Ile Gln Gln Gln Gln Gln Gln Glu Glu Val Leu Gly Ser Leu Asn
                325                 330                 335
```

-continued

```
Asp Gly Val Val Phe Arg Gln Pro Tyr Asn Gln Val Thr Gly Met Asn
            340                 345                 350
Trp Tyr Ser
        355

<210> SEQ ID NO 5
<211> LENGTH: 6
<212> TYPE: PRT
<213> ORGANISM: Solanum lycopersicum

<400> SEQUENCE: 5

Lys Pro Asp Phe Thr Ser
1               5

<210> SEQ ID NO 6
<211> LENGTH: 10
<212> TYPE: PRT
<213> ORGANISM: Solanum lycopersicum

<400> SEQUENCE: 6

Gly Thr Asp Lys Pro Asp Phe Thr Ser Gly
1               5                   10

<210> SEQ ID NO 7
<211> LENGTH: 18
<212> TYPE: PRT
<213> ORGANISM: Solanum lycopersicum

<400> SEQUENCE: 7

Trp Lys Ala Thr Gly Thr Asp Lys Pro Asp Phe Thr Ser Gly Gly Thr
1               5                   10                  15
Gln Lys

<210> SEQ ID NO 8
<211> LENGTH: 23
<212> TYPE: PRT
<213> ORGANISM: Solanum lycopersicum

<400> SEQUENCE: 8

Gly Tyr Trp Lys Ala Thr Gly Thr Asp Lys Pro Asp Phe Thr Ser Gly
1               5                   10                  15
Gly Thr Gln Lys Val Gly Val
            20

<210> SEQ ID NO 9
<211> LENGTH: 111
<212> TYPE: PRT
<213> ORGANISM: Solanum lycopersicum

<400> SEQUENCE: 9

Met Glu Ser Thr Asp Ser Ser Thr Gly Thr Arg His Gln Pro Gln Leu
1               5                   10                  15

Pro Pro Gly Phe Arg Phe His Pro Thr Asp Glu Glu Leu Ile Val His
                20                  25                  30

Tyr Leu Lys Lys Arg Val Ala Gly Ala Pro Ile Pro Val Asp Ile Ile
            35                  40                  45

Gly Glu Ile Asp Leu Tyr Lys Phe Asp Pro Trp Glu Leu Pro Ala Lys
        50                  55                  60

Ala Ile Phe Gly Glu Gln Glu Trp Phe Phe Phe Ser Pro Arg Asp Arg
65                  70                  75                  80
```

```
Lys Tyr Pro Asn Gly Ala Arg Pro Asn Arg Ala Ala Thr Ser Gly Tyr
            85                  90                  95

Trp Lys Ala Thr Gly Thr Asp Lys Pro Asp Phe Thr Ser Gly Gly
            100                 105                 110

<210> SEQ ID NO 10
<211> LENGTH: 136
<212> TYPE: PRT
<213> ORGANISM: Solanum lycopersicum

<400> SEQUENCE: 10

His Gln Pro Gln Leu Pro Pro Gly Phe Arg Phe His Pro Thr Asp Glu
1               5                   10                  15

Glu Leu Ile Val His Tyr Leu Lys Lys Arg Val Ala Gly Ala Pro Ile
            20                  25                  30

Pro Val Asp Ile Ile Gly Glu Ile Asp Leu Tyr Lys Phe Asp Pro Trp
        35                  40                  45

Glu Leu Pro Ala Lys Ala Ile Phe Gly Glu Gln Glu Trp Phe Phe Phe
    50                  55                  60

Ser Pro Arg Asp Arg Lys Tyr Pro Asn Gly Ala Arg Pro Asn Arg Ala
65                  70                  75                  80

Ala Thr Ser Gly Tyr Trp Lys Ala Thr Gly Thr Asp Lys Pro Asp Phe
                85                  90                  95

Thr Ser Gly Gly Thr Gln Lys Val Gly Val Lys Lys Ala Leu Val Phe
            100                 105                 110

Tyr Gly Gly Lys Pro Pro Lys Gly Val Lys Thr Asn Trp Ile Met His
        115                 120                 125

Glu Tyr Arg Val Val Glu Asn Lys
    130                 135

<210> SEQ ID NO 11
<211> LENGTH: 216
<212> TYPE: PRT
<213> ORGANISM: Solanum lycopersicum

<400> SEQUENCE: 11

Met Glu Ser Thr Asp Ser Ser Thr Gly Thr Arg His Gln Pro Gln Leu
1               5                   10                  15

Pro Pro Gly Phe Arg Phe His Pro Thr Asp Glu Glu Leu Ile Val His
            20                  25                  30

Tyr Leu Lys Lys Arg Val Ala Gly Ala Pro Ile Pro Val Asp Ile Ile
        35                  40                  45

Gly Glu Ile Asp Leu Tyr Lys Phe Asp Pro Trp Glu Leu Pro Ala Lys
    50                  55                  60

Ala Ile Phe Gly Glu Gln Glu Trp Phe Phe Phe Ser Pro Arg Asp Arg
65                  70                  75                  80

Lys Tyr Pro Asn Gly Ala Arg Pro Asn Arg Ala Ala Thr Ser Gly Tyr
                85                  90                  95

Trp Lys Ala Thr Gly Thr Asp Lys Pro Asp Phe Thr Ser Gly Gly Thr
            100                 105                 110

Gln Lys Val Gly Val Lys Lys Ala Leu Val Phe Tyr Gly Gly Lys Pro
        115                 120                 125

Pro Lys Gly Val Lys Thr Asn Trp Ile Met His Glu Tyr Arg Val Val
    130                 135                 140

Glu Asn Lys Thr Asn Asn Lys Pro Leu Gly Cys Asp Asn Ile Val Ala
145                 150                 155                 160
```

-continued

```
Asn Lys Lys Gly Ser Leu Arg Leu Asp Asp Trp Val Leu Cys Arg Ile
            165                 170                 175

Tyr Lys Lys Asn Asn Thr Gln Arg Ser Ile Asp Leu His Asp Met
            180                 185                 190

Leu Gly Ser Ile Pro Gln Asn Val Pro Asn Ser Ile Leu Gln Gly Ile
            195                 200                 205

Lys Pro Ser Asn Tyr Gly Thr Ile
    210                 215

<210> SEQ ID NO 12
<211> LENGTH: 20
<212> TYPE: DNA
<213> ORGANISM: Artificial
<220> FEATURE:
<223> OTHER INFORMATION: Nor-F Oligonucleotide

<400> SEQUENCE: 12
actcatcgtc cactacctca                                              20

<210> SEQ ID NO 13
<211> LENGTH: 20
<212> TYPE: DNA
<213> ORGANISM: Artificial
<220> FEATURE:
<223> OTHER INFORMATION: Nor1556 Oligonucleotide

<400> SEQUENCE: 13
tgtcgaacct ctttcggcta                                              20
```

DELAYED FRUIT DETERIORATION ALLELE IN PLANTS AND METHODS OF DETECTION

This application claims the priority benefit of U.S. Provisional Patent Application Ser. No. 61/054,386, filed May 19, 2008, which is hereby incorporated by reference in its entirety.

FIELD OF THE INVENTION

The present invention relates to the delayed fruit deterioration allele in plants and methods of its detection.

BACKGROUND OF THE INVENTION

The textural changes (generically referred to as "softening") that accompany ripening of fleshy fruits are critical determinants of quality and are thus of great commercial importance. Loss of firmness is a major factor limiting transportation and storage of fleshy fruits and it is also associated with the onset of postharvest disease, due to microbial pathogens that penetrate and destroy the fruit flesh. Postharvest fruit quality is dependent on both textural durability during storage and the nutritional and sensory components. The practice of harvesting many fruit prior to full maturity to improve resistance to damage during handling has resulted in crops that typically fail to accumulate a full complement of nutritional compounds, which are essential for optimal quality. Therefore, if the molecular basis of softening could be better understood, and if softening could be uncoupled from other ripening-related processes, fruit could be harvested at a later stage. This in turn would not only make the fruit more resistant to over-softening and less susceptible to microbial infection, but would also dramatically enhance flavor and nutritional content and thus increase commercial value.

A number of tomato ripening mutants have been identified, including rin (ripening inhibitor), nor (non-ripening), alc (alcobaça), and Cnr (Colorless non-ripening), which are impaired in many ripening-related processes and exhibit delayed or impaired softening (Kopeliovitch et al., "Physiology of the Tomato Mutant Alcobaca," *Physiol. Plant.* 48:307-311 (1980); Giovannoni, "Genetic Regulation of Fruit Development and Ripening," *Plant Cell* 16:S170-S180 (2004); U.S. Pat. No. 6,762,347 to Giovannoni et al.; and Manning et al., "A Naturally Occurring Epigenetic Mutation in a Gene Encoding an SBP-box Transcription Factor Inhibits Tomato Fruit Ripening," *Nature Genetics* 38:948-952 (2006)). These mutants have provided insights into several specific aspects of ripening-related metabolism, but their effects on ripening are pleiotropic and some desirable aspects of ripening physiology are adversely affected, which limits their commercial application. For example, the rin mutation, which has been introgressed into a large number of commercial tomato cultivars, slows the rate and/or extent of fruit deterioration, but often has a deleterious effect on color, flavor, and aroma. In this regard, a more desirable tomato cultivar would be one that has reduced or delayed softening, but that exhibits otherwise "normal" ripening, with the attending quality metrics.

The present invention is directed to overcoming these and other deficiencies in the art.

SUMMARY OF THE INVENTION

A first aspect of the present invention is directed to an isolated nucleic acid molecule comprising a nucleotide sequence at least 90% identical to a nucleotide sequence encoding a protein having the amino acid sequence of SEQ ID NO:4, where the protein has an aspartic acid (Asp) at amino acid position 106.

A second aspect of the present invention is directed to an isolated nucleic acid molecule encoding an amino acid sequence selected from the group consisting of SEQ ID NO:6, SEQ ID NO:7, SEQ ID NO:8, SEQ ID NO:9, SEQ ID NO:10, and SEQ ID NO:11.

A third aspect of the present invention is directed to a vector containing a nucleic acid molecule according to the present invention.

A fourth aspect of the present invention is directed to a transgenic plant with reduced or delayed softening and deterioration of fruit compared to its respective wild-type plants, the transgenic plant comprising a vector according to the present invention.

A fifth aspect of the present invention is directed to a method of genetic screening for plants having reduced or delayed softening and deterioration of fruit. This method involves identifying a plant or plant cell containing a NOR gene, where the NOR gene comprises a nucleic acid molecule encoding the amino acid sequence of SEQ ID NO:4.

A sixth aspect of the present invention is directed to an isolated oligonucleotide comprising a nucleotide sequence selected from SEQ ID NO:12 and SEQ ID NO:13.

A seventh aspect of the present invention is directed to a kit for detecting a NOR gene in a plant, said kit comprising an oligonucleotide comprising the nucleotide sequence of SEQ ID NO:12 and/or SEQ ID NO:13.

An eighth aspect of the present invention is directed to a method of genetic screening. This method involves identifying a nucleotide sequence linked to a NOR gene, where the NOR gene comprises a nucleic acid molecule encoding the amino acid sequence of SEQ ID NO:4. The nucleotide sequence is utilized as a marker to screen or map the NOR gene.

A ninth aspect of the present invention is directed to a method of imparting to a plant the dfd trait. This method involves transforming a plant with the vector of the present invention to impart the dfd trait.

According to the present invention, a genetic mapping strategy was used to identify a single nucleotide polymorphism ("SNP") that segregated with the dfd trait (reduced softening or prolonged postharvest shelf life). Accordingly, one aspect of the present invention relates to a method for identifying specific DNA sequences associated with dfd in plants and the use of isolated nucleic acid fragments and recombinant constructs utilizing this sequence to alter fruit ripening in tomato and other horticultural crops.

DETAILED DESCRIPTION OF THE INVENTION

Figure 1:
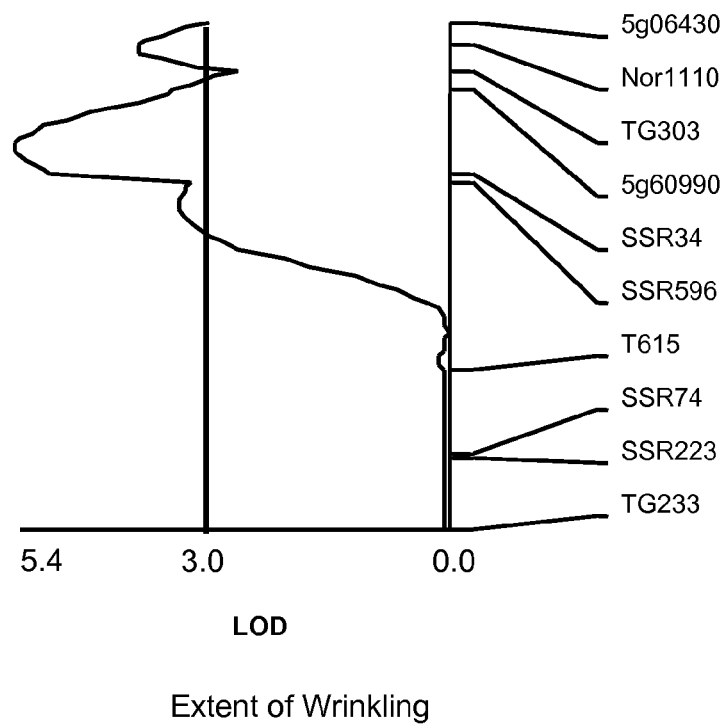
FIG. 1 is a graph showing LOD score values of the dfd F2 population plotted against the genetic map of the short arm of chromosome 10.

Delayed fruit deterioration ("dfd") is a tomato cultivar/ecotype with fruit exhibiting unusually long postharvest shelf life, as evidenced by longer maintenance of firmness, reduced water loss, and reduced susceptibility to postharvest pathogen infection, compared to what is typically seen in tomato fruit (Saladié et al, "A Re-evaluation of the Key Factors That Contribute to Tomato Fruit Softening and Integrity," *Plant Physiology* 144:1012-1028 (2007), which is hereby incorporated by reference in its entirety). Importantly, dfd fruit apparently undergo otherwise normal ripening, unlike all known non-softening tomato mutants reported to date, such as rin, nor, and ale (Saladié et al, "A Re-evaluation of the Key Factors That Contribute to Tomato Fruit Softening and Integrity," *Plant Physiology* 144:1012-1028 (2007), which is hereby incorporated by reference in its entirety). Moreover, dfd fruit ripen in the homozygous state, unlike other ripening mutants, which are used in hybrids.

As described herein, the present invention is based on the discovery of the specific DNA sequence that is associated with prolonged shelf life of fruit from dfd. Accordingly, the present invention is directed to isolated nucleic acid molecules and recombinant constructs utilizing these molecules to alter fruit ripening in tomato and other horticultural crops.

A first aspect of the present invention is directed to an isolated nucleic acid molecule comprising a nucleotide sequence at least 90% identical to a nucleotide sequence encoding a protein having the amino acid sequence of SEQ ID NO:4, where the protein has an aspartic acid (Asp) at amino acid position 106.

The polypeptide encoded by the NOR gene has the amino acid sequence according to NCBI Accession No. AAU43922 (SEQ ID NO:1), as follows.

```
Met Glu Ser Thr Asp Ser Ser Thr Gly Thr Arg His Gln Pro Gln Leu
1               5                   10                  15

Pro Pro Gly Phe Arg Phe His Pro Thr Asp Glu Glu Leu Ile Val His
                20                  25                  30

Tyr Leu Lys Lys Arg Val Ala Gly Ala Pro Ile Pro Val Asp Ile Ile
            35                  40                  45

Gly Glu Ile Asp Leu Tyr Lys Phe Asp Pro Trp Glu Leu Pro Ala Lys
        50                  55                  60

Ala Ile Phe Gly Glu Gln Glu Trp Phe Phe Phe Ser Pro Arg Asp Arg
65                  70                  75                  80

Lys Tyr Pro Asn Gly Ala Arg Pro Asn Arg Ala Ala Thr Ser Gly Tyr
                85                  90                  95

Trp Lys Ala Thr Gly Thr Asp Lys Pro Val Phe Thr Ser Gly Gly Thr
                100                 105                 110

Gln Lys Val Gly Val Lys Lys Ala Leu Val Phe Tyr Gly Gly Lys Pro
        115                 120                 125

Pro Lys Gly Val Lys Thr Asn Trp Ile Met His Glu Tyr Arg Val Val
        130                 135                 140

Glu Asn Lys Thr Asn Asn Lys Pro Leu Gly Cys Asp Asn Ile Val Ala
145                 150                 155                 160

Asn Lys Lys Gly Ser Leu Arg Leu Asp Asp Trp Val Leu Cys Arg Ile
                165                 170                 175

Tyr Lys Lys Asn Asn Thr Gln Arg Ser Ile Asp Asp Leu His Asp Met
            180                 185                 190

Leu Gly Ser Ile Pro Gln Asn Val Pro Asn Ser Ile Leu Gln Gly Ile
        195                 200                 205

Lys Pro Ser Asn Tyr Gly Thr Ile Leu Leu Glu Asn Glu Ser Asn Met
    210                 215                 220

Tyr Asp Gly Ile Met Asn Asn Thr Asn Asp Ile Ile Asn Asn Asn
225                 230                 235                 240

Arg Ser Ile Pro Gln Ile Ser Ser Lys Arg Thr Met His Gly Gly Leu
                245                 250                 255

Tyr Trp Asn Asn Asp Glu Ala Thr Thr Thr Thr Thr Ile Asp Arg
            260                 265                 270

Asn His Ser Pro Asn Thr Lys Arg Phe Leu Val Gln Asn Asn Glu Asp
        275                 280                 285

Asp Gly Leu Asn Met Asn Asn Ile Ser Arg Ile Thr Asn His Gln Gln
    290                 295                 300

Ser Ser Ser Ile Ala Asn Phe Leu Ser Gln Phe Pro Gln Asn Pro Ser
305                 310                 315                 320

Ile Gln Gln Gln Gln Gln Gln Glu Glu Val Leu Gly Ser Leu Asn
                325                 330                 335
```

```
Asp Gly Val Val Phe Arg Gln Pro Tyr Asn Gln Val Thr Gly Met Asn
            340                 345                 350

Trp Tyr Ser
        355
```

The cDNA sequence corresponding to the NOR gene (NCBI Accession No. AY573803) has the nucleotide sequence of SEQ ID NO:2, as follows.

```
ctaaattcct tcttgtttat cattttctct cttcccaaaa aaaaaatccc aaaatttaat      60
cataatacaa ttcgaattta tcaacctcgt actacgtaca tattttgtt  ggtacgtaaa     120
atactgaatt caggtcaact caaacatcgt aaattgtgat ttctttatgg aaagtacgga     180
ttcatcaacc gggacacgtc atcagcctca actcccaccg gggtttcgat tccacccgac     240
ggacgaagaa ctcatcgtcc actacctcaa aaaacgagtc gccggcgctc cgattccggt     300
ggatattatt ggtgaaattg atctttataa gtttgatcca tgggaactcc ctgctaaggc     360
aatattcgga gagcaagaat ggttattttt tagtccaaga gatagaaaat atcctaacgg     420
ggcgaggcca aatcgggctg caacatcggg ttattggaag gctaccggaa ccgacaagcc     480
ggttttact  tccggtggaa cacaaaaggt tggggtaaaa aaggcgctcg tttttacgg      540
cggtaaacca ccaaaagggg taaaaactaa ttggatcatg catgaataca gagttgtaga     600
aaataaaaca aataacaagc cacttggttg tgataatatt gttgccaaca aaaaaggatc     660
tttgaggcta gatgattggg ttttatgtcg aatttacaag aagaataaca cacaaaggtc     720
catagatgat ttgcatgata tgttgggatc gataccacaa aatgtaccaa attcaatatt     780
acaaggaata aagccttcaa actatggtac aatattgctc gaaaatgaat cgaatatgta     840
cgatggaatt atgaataaca cgaacgatat tatcaacaat aataatagat ccattccaca     900
aatatcgtca aagagaacga tgcatggagg tttgtattgg aataacgacg aagcaacaac     960
aacaacaaca actattgata ggaaccattc tccaaataca aaaaggttcc ttgttgagaa    1020
caacgaggac gatggactta acatgaataa tatttcgcga attacaaatc atgaacaaag    1080
tagctccatt gccaatttcc tgagccagtt tcctcaaaat ccttcgattc aacaacaaca    1140
acaacaacaa gaagaagtat tgggatctct taatgatggg gtcgtctttc gacaaccttc    1200
taatcaagtt actggcatga attggtactc ttaaagatat aaaaaggcaa aaaatagtta    1260
gccctgtaaa atcaatcgat caatcaatca tagatatatt atatatggat tatcttctat    1320
tttactttta gttagaatta atatatagaa tatcttctat ctcacattaa caaataagaa    1380
catttataac aaaaaaaaaa aaaaaaaaaa aaaaaaaaaa aaa                      1423
```

The genomic sequence of NOR (NCBI Accession No. AY573803), referred to herein as SEQ ID NO:3, has the following nucleotide sequence.

```
ctaaattcct tcttgtttat cattttctct cttcccaaaa aaaaatccca aaatttaatc      60
ataatacaat tcgaatttat caacctcgta ctacgtacat attttgttg  gtacgtaaaa    120
tactgaattc aggtcaactc aaacatcgta aattgtgatt tctttatgga aagtacggat    180
tcatcaaccg ggacacgtca tcagcctcaa ctcccaccgg ggtttcgatt ccacccgacg    240
gacgaagaac tcatcgtcca ctacctcaaa aaacgagtcg ccggcgctcc gattccggtg    300
gatattattg gtgaaattga tctttataag tttgatccat gggaactccc tggtactatt    360
ttcaccacta tactatattt tcttgcccta taacttatat atagggggaaa aagatcggag   420
```

-continued

```
tcagcgatga acaattattg tgtctaaatt aaattttaaa tatgcaatag attggtgacg      480
aatttcgttg ctaattaatt ttttagtgat aaattaatat ttttcccctt tttaatcttc      540 atgttttta tcacaaagtt ttctatgacc aactataaa gatttgaact cgatcaattt        600 ttttttttaga atgaatgaac ttatgttata tatagtgata ttttaaatgc ttttttatat    660
tttcaaaaga tatccacgat aacgtgtaaa aagtgaattt gcaaaaaaaa aaatgtagta      720 cctttattt aattttattg tagataattt agattttaat tttgaatttg tttaattaa        780 attctgaatc gtataatatt tatttaattt ctattttttg agttttttt tggagggtgc       840 ttaaaaagta gtattcacaa atataaagta gtggacaaac ataaagtagt ggacccataa      900
tttatttttt taaaaattat attaaaacta tttgttaagt ttaaattctg aattatcttc      960
ttatcatgtg tttaacgcag ctaaggcaat attcggagag caagaatggt tcttttttag     1020
tccaagagat agaaaatatc ctaacggggc gaggccaaat cgggctgcaa catcgggtta    1080
ttggaaggct accggaaccg acaagccggt ttttacttcc ggtggaacac aaaaggttgg     1140
ggtaaaaaag gcgctcgttt tttacggcgg taaaccacca aaaggggtaa aaactaattg     1200
gatcatgcat gaatacagag ttgtagaaaa taaaacaaat aacaagccac ttggttgtga     1260
taatattgtt gccaacaaaa aaggatcttt gagggtaagt cctaaatttt gcatcgaaac     1320
taatttctct atcgtatcag atagggataa gatatacgta tactctaatc tccttgaacc     1380
ccacaagtac tatactagat atgttgttgt tgtagatgac ttgattcaac tttcaaattt     1440
ttgatgaaaa tgtttaagtt atatatacat atatatatag gcggagctaa aaatttcgat    1500
aaggggtttt aaatcgaaa aaatggatat acgaaatagc cgaaagaggt tcgacataga     1560 ttatttaac catataaaaa taatacaatt ttcatatata tatacgcgtg gttaatatga     1620 ggaatattt atactattaa tgtactttaa ccaggggcgg ctctagagtt gatgaaccct     1680
ctcagcgaaa atttacgttg tatatttaag gtacctttta ataattttg tatttatata      1740 ttaattttga acctcttaaa tataagatta gacgttgact tagtggtttc aggggttcaa    1800
atcactattc ttttttttcct aacccccta atgaaaatcc tgaatcggcc actaacttta    1860
actggttata gaaggttaat cttactagaa aaaagcatga aattctaacc gacaaagatg    1920 agtcgccca gttagataag acgtttaaat tgggacggat agagttactt tattttttcac     1980 tgtcatatgt tactatatat tgacacttca cttaaagagt tatcatatcg atatttttac    2040
tattagtgta cataacacaa actcgaataa attcaatgtt tcattagcta gttaattagt    2100
ctaacttttt taaaaaaaaa tatttttctt actccacact attttatttt attttttttgc   2160 agctagatga ttgggtttta tgtcgaattt acaagaagaa taacacacaa aggtccatag    2220
atgatttgca tgatatgttg ggatcgatac cacaaaatgt accaaattca atattacaag    2280
gaataaagcc ttcaaactat ggtacaatat tgctcgaaaa tgaatcgaat atgtacgatg    2340
gaattatgaa taacacgaac gatattatca acaataataa tagatccatt ccacaaatat    2400
cgtcaaagag aacgatgcat ggaggtttgt attggaataa cgacgaagca acaacaacaa    2460
caacaactat tgataggaac cattctccaa atacaaaaag gttccttgtt gagaacaacg    2520
aggacgatgg acttaacatg aataatattt cgcgaattac aaatcatgaa caaagtagct    2580
ccattgccaa tttcctgagc cagtttcctc aaaatccttc gattcaacaa caacaacaac    2640
aacaagaaga agtattggga tctcttaatg atggggtcgt ctttcgacaa ccttataatc    2700
aagttactag catgaattgg tactcttaaa gatataaaaa ggcaaaaaat agttagccct    2760
gtaaaatcaa tcgatcaatc aatcatagat atattatata tggatttcgt tatattttac    2820
```

-continued

```
ttttagttag aattaatata tagaatatct tctatctcac attaacaaat aagaacattt    2880
ataac                                                                2885
```

As referred to herein, SEQ ID NO:4 corresponds to the polypeptide encoded by the NOR gene, but where the polypeptide has an aspartic acid (Asp) at amino acid position 106, and has the following nucleic acid sequence.

```
Met Glu Ser Thr Asp Ser Ser Thr Gly Thr Arg His Gln Pro Gln Leu
1               5                   10                  15

Pro Pro Gly Phe Arg Phe His Pro Thr Asp Glu Glu Leu Ile Val His
            20                  25                  30

Tyr Leu Lys Lys Arg Val Ala Gly Ala Pro Ile Pro Val Asp Ile Ile
            35                  40                  45

Gly Glu Ile Asp Leu Tyr Lys Phe Asp Pro Trp Glu Leu Pro Ala Lys
        50                  55                  60

Ala Ile Phe Gly Glu Gln Glu Trp Phe Phe Ser Pro Arg Asp Arg
65                  70                  75                  80

Lys Tyr Pro Asn Gly Ala Arg Pro Asn Arg Ala Ala Thr Ser Gly Tyr
                85                  90                  95

Trp Lys Ala Thr Gly Thr Asp Lys Pro Asp Phe Thr Ser Gly Gly Thr
            100                 105                 110

Gln Lys Val Gly Val Lys Lys Ala Leu Val Phe Tyr Gly Gly Lys Pro
            115                 120                 125

Pro Lys Gly Val Lys Thr Asn Trp Ile Met His Glu Tyr Arg Val Val
            130                 135                 140

Glu Asn Lys Thr Asn Asn Lys Pro Leu Gly Cys Asp Asn Ile Val Ala
145                 150                 155                 160

Asn Lys Lys Gly Ser Leu Arg Leu Asp Asp Trp Val Leu Cys Arg Ile
                165                 170                 175

Tyr Lys Lys Asn Asn Thr Gln Arg Ser Ile Asp Asp Leu His Asp Met
            180                 185                 190

Leu Gly Ser Ile Pro Gln Asn Val Pro Asn Ser Ile Leu Gln Gly Ile
            195                 200                 205

Lys Pro Ser Asn Tyr Gly Thr Ile Leu Leu Glu Asn Glu Ser Asn Met
            210                 215                 220

Tyr Asp Gly Ile Met Asn Asn Thr Asn Asp Ile Ile Asn Asn Asn Asn
225                 230                 235                 240

Arg Ser Ile Pro Gln Ile Ser Ser Lys Arg Thr Met His Gly Gly Leu
            245                 250                 255

Tyr Trp Asn Asn Asp Glu Ala Thr Thr Thr Thr Thr Ile Asp Arg
            260                 265                 270

Asn His Ser Pro Asn Thr Lys Arg Phe Leu Val Glu Asn Asn Glu Asp
            275                 280                 285

Asp Gly Leu Asn Met Asn Asn Ile Ser Arg Ile Thr Asn His Glu Gln
            290                 295                 300

Ser Ser Ser Ile Ala Asn Phe Leu Ser Gln Phe Pro Gln Asn Pro Ser
305                 310                 315                 320

Ile Gln Gln Gln Gln Gln Gln Glu Glu Val Leu Gly Ser Leu Asn
                325                 330                 335

Asp Gly Val Val Phe Arg Gln Pro Tyr Asn Gln Val Thr Gly Met Asn
                340                 345                 350

Trp Tyr Ser
        355
```

The amino acid substitution from valine (Val) to aspartic acid (Asp) at position 106 of the polypeptide encoded by the NOR gene in SEQ ID NO:4 arises from a single nucleotide polymorphism (t→a) at position 1110 of the NOR genomic sequence (SEQ ID NO:3) and position 483 of the cDNA sequence (SEQ ID NO:2). As described in further detail infra, this mutation in the NOR gene (referred to herein as the NOR1110 allele of dfd) abolishes a digestion site by the BsrFI restriction enzyme (gceggt→gccgga).

Another aspect of the present invention relates to isolated nucleic acid molecules having a nucleotide sequence that is at least 91% identical, at least 92% identical, at least 93% identical, at least 94% identical, at least 95% identical, at least 96% identical, at least 97% identical, at least 98% identical, or at least 99% identical to a nucleotide sequence encoding a protein having the amino acid sequence of SEQ ID NO:4, where the protein has an aspartic acid (Asp) at amino acid position 106.

In one embodiment, the isolated nucleic acid molecule has a nucleotide sequence that is at least 90-95% identical to a nucleotide sequence encoding a protein having the amino acid sequence of SEQ ID NO:4, where the protein includes the amino acid sequence of SEQ ID NO:5, as follows.

```
Lys Pro Asp Phe Thr Ser
1               5
```

The determination of percent identity, i.e., sequence similarity, between two nucleotide (or amino acid) sequences can be accomplished using a mathematical algorithm. A preferred, non-limiting example of a mathematical algorithm utilized for the comparison of two sequences is the algorithm of Karlin et al., "Methods for Assessing the Statistical Significance of Molecular Sequence Features by Using General Scoring Schemes," *Proc. Natl. Acad. Sci.* 87:2264-2268 (1990), which is hereby incorporated by reference in its entirety, modified as in Karlin et al., "Applications and Statistics for Multiple High-Scoring Segments in Molecular Sequences," *Proc. Natl. Acad. Sci.* 90:5873-5877 (1993), which is hereby incorporated by reference in its entirety. Another non-limiting example of a mathematical algorithm utilized for the comparison of sequences is the algorithm of Myers et al., CABIOS (1989), which is hereby incorporated by reference in its entirety. Such an algorithm can be incorporated into the ALIGN program (version 2.0) which is part of the CGC sequence alignment software package. Additional algorithms for sequence analysis are known in the art and include ADVANCE and ADAM as described in Torellis et al., "ADVANCE and ADAM: Two Algorithms for the Analysis of Global Similarity Between Homologous Informational Sequences," *Comput. Appl. Biosci.* 10:3-5 (1994), which is hereby incorporated by reference in its entirety, and FASTA described in Pearson et al., "Improved Tools for Biological Sequence Comparison," *Proc. Natl. Acad. Sci.* 85:2444-8 (1988), which is hereby incorporated by reference in its entirety.

Another aspect of the present invention is directed to an isolated nucleic acid molecule encoding an amino acid sequence selected from:

```
SEQ ID NO: 6:
Gly Thr Asp Lys Pro Asp Phe Thr Ser Gly
1               5                   10

SEQ ID NO: 7:
Trp Lys Ala Thr Gly Thr Asp Lys Pro Asp Phe Thr Ser Gly Gly Thr
1               5                   10                  15

Gln Lys

SEQ ID NO: 8:
Gly Tyr Trp Lys Ala Thr Gly Thr Asp Lys Pro Asp Phe Thr Ser Gly
1               5                   10                  15

Gly Thr Gln Lys Val Gly Val
              20

SEQ ID NO: 9:
Met Glu Ser Thr Asp Ser Ser Thr Gly Thr Arg His Gln Pro Gln Leu
1               5                   10                  15

Pro Pro Gly Phe Arg Phe His Pro Thr Asp Glu Glu Leu Ile Val His
              20                  25                  30

Tyr Leu Lys Lys Arg Val Ala Gly Ala Pro Ile Pro Val Asp Ile Ile
              35                  40                  45

Gly Glu Ile Asp Leu Tyr Lys Phe Asp Pro Trp Glu Leu Pro Ala Lys
       50                  55                  60

Ala Ile Phe Gly Glu Gln Glu Trp Phe Phe Ser Pro Arg Asp Arg
65                  70                  75                  80

Lys Tyr Pro Asn Gly Ala Arg Pro Asn Arg Ala Ala Thr Ser Gly Tyr
                  85                  90                  95

Trp Lys Ala Thr Gly Thr Asp Lys Pro Asp Phe Thr Ser Gly Gly
                  100                 105                 110
```

-continued

SEQ ID NO: 10:
His Gln Pro Gln Leu Pro Pro Gly Phe Arg Phe His Pro Thr Asp Glu
1               5                   10                  15

Glu Leu Ile Val His Tyr Leu Lys Lys Arg Val Ala Gly Ala Pro Ile
            20                  25                  30

Pro Val Asp Ile Ile Gly Glu Ile Asp Leu Tyr Lys Phe Asp Pro Trp
        35                  40                  45

Glu Leu Pro Ala Lys Ala Ile Phe Gly Glu Gln Glu Trp Phe Phe Phe
50                  55                  60

Ser Pro Arg Asp Arg Lys Tyr Pro Asn Gly Ala Arg Pro Asn Arg Ala
65                  70                  75                  80

Ala Thr Ser Gly Tyr Trp Lys Ala Thr Gly Thr Asp Lys Pro Asp Phe
                85                  90                  95

Thr Ser Gly Gly Thr Gln Lys Val Gly Val Lys Lys Ala Leu Val Phe
            100                 105                 110

Tyr Gly Gly Lys Pro Pro Lys Gly Val Lys Thr Asn Trp Ile Met His
        115                 120                 125

Glu Tyr Arg Val Val Glu Asn Lys
130                 135

SEQ ID NO: 11:
Met Glu Ser Thr Asp Ser Ser Thr Gly Thr Arg His Gln Pro Gln Leu
1               5                   10                  15

Pro Pro Gly Phe Arg Phe His Pro Thr Asp Glu Glu Leu Ile Val His
            20                  25                  30

Tyr Leu Lys Lys Arg Val Ala Gly Ala Pro Ile Pro Val Asp Ile Ile
        35                  40                  45

Gly Glu Ile Asp Leu Tyr Lys Phe Asp Pro Trp Glu Leu Pro Ala Lys
50                  55                  60

Ala Ile Phe Gly Glu Gln Glu Trp Phe Phe Phe Ser Pro Arg Asp Arg
65                  70                  75                  80

Lys Tyr Pro Asn Gly Ala Arg Pro Asn Arg Ala Ala Thr Ser Gly Tyr
                85                  90                  95

Trp Lys Ala Thr Gly Thr Asp Lys Pro Asp Phe Thr Ser Gly Gly Thr
            100                 105                 110

Gln Lys Val Gly Val Lys Lys Ala Leu Val Phe Tyr Gly Gly Lys Pro
        115                 120                 125

Pro Lys Gly Val Lys Thr Asn Trp Ile Met His Glu Tyr Arg Val Val
130                 135                 140

Glu Asn Lys Thr Asn Asn Lys Pro Leu Gly Cys Asp Asn Ile Val Ala
145                 150                 155                 160

Asn Lys Lys Gly Ser Leu Arg Leu Asp Asp Trp Val Leu Cys Arg Ile
                165                 170                 175

Tyr Lys Lys Asn Asn Thr Gln Arg Ser Ile Asp Asp Leu His Asp Met
            180                 185                 190

Leu Gly Ser Ile Pro Gln Asn Val Pro Asn Ser Ile Leu Gln Gly Ile
        195                 200                 205

Lys Pro Ser Asn Tyr Gly Thr Ile
210                 215

It will be appreciated by those of ordinary skill in the art that, as a result of the degeneracy of the genetic code, there are many nucleotide sequences that encode a polypeptide as described supra. Some of these polynucleotides bear minimal homology to the nucleotide sequence of any native gene. Nonetheless, polynucleotides that vary due to differences in codon usage are specifically contemplated by the present invention. Polynucleotides may be prepared using any of a variety of techniques known in the art.

A further aspect of the present invention is directed to a vector containing a nucleic acid molecule of the present invention. Generally, this involves inserting a nucleic acid molecule of the present invention into an expression system to which the nucleic acid molecule is heterologous (i.e., not normally present), and where the nucleic acid molecule is operably linked to 5' and 3' transcriptional and translational regulatory elements (e.g., promoter, enhancer, suppressor, transcription terminator, etc.) to allow for expression of the nucleic acid molecule in a host.

Another aspect of the present invention is directed to a transgenic plant with reduced or delayed softening and deterioration of fruit compared to its respective wild-type plants. In order to transgenically express a nucleic acid of the present invention (e.g., the mutant NOR gene) in plants, transgenic plants carrying the isolated nucleic acid molecule of the present invention are produced by transforming a plant with a transgene (e.g., a chimeric DNA) construct that expresses a nucleic acid of the present invention.

In order to express the nucleic acid molecule of the present invention (e.g., the mutant NOR gene) from the transgene, the construct should include a plant specific promoter. The promoter should ensure that the foreign gene is expressed in the plant. The promoter can be chosen so that the expression occurs only in specified tissues, at a determined time point in the plant's development or at a time point determined by outside influences. The promoter can be homologous or heterologous to the plant. Suitable promoters include, e.g., the RUBISCO small subunit promoter, tissue-specific promoters, the promoter of the 35S RNA of the cauliflower mosaic virus (U.S. Pat. No. 5,034,322 to Rogers et al., which is hereby incorporated by reference in its entirety), the enhanced 35S promoter (U.S. Pat. No. 5,106,739 to Comai et al., which is hereby incorporated by reference in its entirety), the dual S35 promoter, the FMV promoter from figwort mosaic virus (U.S. Pat. No. 5,378,619 to Rogers, which is hereby incorporated by reference in its entirety), the RI T-DNA promoter (U.S. Pat. No. 5,466,792 to Slightom et al., which is hereby incorporated by reference in its entirety), the octopine T-DNA promoter (U.S. Pat. No. 5,428,147 to Barker et al., which is hereby incorporated by reference in its entirety), the alcohol dehydrogenase 1 promoter (Callis et al., "Introns Increase Gene Expression in Cultured Maize Cells," *Genes Dev.* 1(10): 1183-200 (1987), which is hereby incorporated by reference in its entirety), the patatin promoter B33 (Rocha-Sosa et al., "Both Developmental and Metabolic Signals Activate the Promoter of a Class I Patatin Gene," *EMBO J.* 8(1):23-9 (1989), which is hereby incorporated by reference in its entirety), the E8 promoter (Deikman et al., "Interaction of a DNA Binding Factor with the 5'-Flanking Region of an Ethylene-responsive Fruit Ripening Gene from Tomato," *EMBO J.* 7(11):3315-20 (1988) and He et al., "Assessment of the Utility of the Tomato Fruit-specific E8 Promoter for Driving Vaccine Antigen Expression," *Genetica* 133:207-214 (2007), which are hereby incorporated by reference in its entirety), the beta-conglycin promoter (Tierney et al., "Isolation and Characterization of a Genomic Clone Encoding the β-Subunit of β-Conglycinin," *Planta* 172(3):356-63 (1987), which is hereby incorporated by reference in its entirety), the acid chitinase promoter (Samac et al., "Isolation and Characterization of the Genes Encoding Basic and Acidic Chitinase in *Arabidopsis thaliana*," *Plant Physiol.* 93(3):907-14 (1990), which is hereby incorporated by reference in its entirety), the *Arabidopsis* histone H4 promoter (U.S. Pat. No. 5,491,288 to Chaubet et al., which is hereby incorporated by reference in its entirety), or the recombinant promoter for expression of genes in monocots (U.S. Pat. No. 5,290,924 to Last et al., which is hereby incorporated by reference in its entirety).

Preferred promoters include the RUBISCO small subunit promoter, the 35S promoters, fiber enhanced promoters, vascular cell enhanced promoters, stem cell enhanced promoters, or seed enhanced promoters. Such promoters may ensure expression in a tissue specific or tissue-enhanced manner, but may allow expression in other cell types. For example it may ensure enhanced expression in photosynthetically active tissues (Worrell et al., "Expression of a Maize Sucrose Phosphate Synthase in Tomato Alters Leaf Carbohydrate Partitioning," *Plant Cell* 3(10):1121-30 (1991), which is hereby incorporated by reference in its entirety) or other mesophyll-cell-specific promoters (Datta et al., "Constitutive and Tissue-specific Differential Expression of the CryIA(b) Gene in Transgenie Rice Plants Conferring Resistance to Rice Insect Pest," *Theor. Appl. Genet.* 97:20-30 (1998), which is hereby incorporated by reference in its entirety). Other promoters can be used that ensure expression only in specified organs, such as the leaf, root, tuber, seed, stem, fruit, or flower, or specified cell types such as parenchyma, epidermal, or vascular cells. One example of a tissue-specific promoter is the RB7 promoter that is root specific (U.S. Pat. No. 5,459,252 to Conkling et al., which is hereby incorporated by reference in its entirety). Such promoters may be used either alone or in combination to optimize over-expression in the most desirable set of tissues or organs.

A particularly preferred promoter of the present invention is the fruit specific E8 promoter (He et al., "Assessment of the Utility of the Tomato Fruit-specific E8 Promoter for Driving Vaccine Antigen Expression," *Genetica* 133:207-214 (2007), which is hereby incorporated by reference in its entirety).

In one embodiment of the present invention, the transgene is stably integrated into the genome of the non-transformed plant. When a plant is transformed by *Agrobacterium* mediated transformation, a portion of the Ti plasmid integrates into the plant genome and is stably passed on to future generations of plant cells.

Numerous methods exist for transforming plant cells. The preferred methods include electroporation, *Agrobacterium* mediated transformation, biolistic gene transformation, chemically mediated transformation, or microinjection.

The vector described above can be microinjected directly into plant cells by use of micropipettes to transfer mechanically the recombinant DNA (Crossway et al., "Integration of Foreign DNA Following Microinjection of Tobacco Mesophyll Protoplasts," *Mol. Gen. Genetics* 202(2):179-85 (1986), which is hereby incorporated by reference in its entirety). The genetic material may also be transferred into the plant cell using polyethylene glycol (Krens et al., "In vitro Transformation of Plant Protoplasts with Ti-plasmid DNA," *Nature* 296: 72-4 (1982), which is hereby incorporated by reference in its entirety).

Another approach to transforming plant cells with an isolated nucleic acid molecule of the present invention is particle bombardment (also known as biolistic transformation) of the host cell. This can be accomplished in one of several ways. The first involves propelling inert or biologically active particles at cells. This technique is disclosed in U.S. Pat. Nos.

4,945,050; 5,036,006; and 5,100,792; which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Yet another method of introduction is fusion of protoplasts with other entities, either minicells, cells, lysosomes or other fusible lipid-surfaced bodies (Fraley et al., "Liposome-mediated Delivery of Tobacco Mosaic Virus RNA into Tobacco Protoplasts: A Sensitive Assay for Monitoring Liposome-protoplast Interactions," Proc. Nat'l Acad. Sci. USA 79(6): 1859-63 (1982), which is hereby incorporated by reference in its entirety).

The isolated nucleic acid molecule may also be introduced into the plant cells by electroporation (Fromm et al., "Expression of Genes Transferred into Monocot and Dicot Plant Cells by Electroporation," Proc. Nat'l Acad. Sci. USA 82(17):5824-8 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the isolated nucleic acid molecule of the present invention into plant cells is to infect a plant cell with *Agrobacterium tumefaciens* or *A. rhizogenes* previously transformed with the isolated nucleic acid molecule. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25-28° C.

*Agrobacterium* is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome (Schell, "Transgenic Plants as Tools to Study the Molecular Organization of Plant Genes," Science 237(4819):1176-83 (1987), which is hereby incorporated by reference in its entirety).

After transformation, whole transformed plants can be recovered. If transformed seeds were produced directly, these can be selected by germination on selection medium and grown into plants (Clough & Bent, "Floral Dip: A Simplified Method for *Agrobacterium*-mediated Transformation of *Arabidopsis thaliana*," Plant J. 16(6):735-43 (1998), which is hereby incorporated by reference in its entirety). If transformed pollen was produced directly, this can be used for in vivo pollination followed by selection of transformed seeds (Touraev et al., "Plant Male Germ Line Transformation," Plant J. 12(4):949-56 (1997), which is hereby incorporated by reference in its entirety). If meristems were transformed, these can be grown into plants in culture then transferred to soil (Gould et al., "Regeneration of *Gossypium hirsutum* and *G. barbadense* from Shoot Apex Tissues for Transformation," Plant Cell Rep. 10(1):12-16 (1991), which is hereby incorporated by reference in its entirety).

If protoplasts or explants were transformed, plants can be regenerated. Plant regeneration from cultured protoplasts is described in DAVID EVANS ET AL., I HANDBOOK OF PLANT CELL CULTURE (1983); I CELL CULTURE AND SOMATIC CELL GENETICS OF PLANTS (Indra K. Vasil ed., 1984); and III CELL CULTURE AND SOMATIC CELL GENETICS OF PLANTS (Indra K. Vasil ed., 1986), which are hereby incorporated by reference in their entirety. Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

It is known that practically all plants can be regenerated from cultured cells or tissues.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedures with the presence of the isolated nucleic acid molecule encoding, e.g., a mutant NOR gene of the present invention. Alternatively, transgenic seeds are recovered from the transgenic plants. These seeds can then be planted in the soil and cultivated using conventional procedures to produce transgenic plants.

Suitable transgenic plants include, without limitation, plants with fleshy fruit, plants of the Solanaceae family, plants of the Rosaceae family, tomato, pepper, strawberry, eggplant, paprika, chili pepper, bell pepper, tomatillo, potato, and sweet potato.

Another aspect of the present invention is directed to a method of imparting to a plant the dfd trait. This method involves transforming a plant with a vector of the present invention via procedures described herein to impart the dfd trait.

Another aspect of the present invention is directed to the fruit of a transgenic plant of the present invention.

Isolated nucleic acid molecules of the present invention can be useful in screen assays as molecular markers for particular phenotypes (e.g., dfd). Accordingly, a further aspect of the present invention is directed to a method of genetic screening for plants having reduced or delayed softening and deterioration of the fruit. This method involves identifying a plant or plant cell containing a NOR gene, where the NOR gene comprises the nucleic acid molecule encoding the amino acid sequence of SEQ ID NO:4. Reduced or delayed softening and deterioration of the fruit may include that which results from microbial infection.

According to this method, the identifying step may be performed on a sample isolated from a plant, a plant seedling, a plant tissue culture, or a plant cell culture. The sample may also be from plant tissue or a plant seed.

In the methods of the invention, the NOR1110 allele may be identified by any genotyping assay that relies on the detection of the presence or absence of the single nucleotide polymorphism characteristic of the NOR1110 allele as described herein. Such methods include DNA sequencing, PCR assays, single base pair extension assays, ligase detection reaction, and ligase chain reaction.

DNA sequencing is a technique utilized to determine the sequence of nucleotides in a particular DNA molecule. Typical sequencing reactions include appropriate sequencing buffers, nucleotides, dideoxy nucleotides, DNA polymerase and one or more oligonucleotide primers.

The polymerase chain reaction (PCR) is a technique utilized to amplify DNA and can be utilized to detect differences in sequences. Typical PCR reactions include appropriate PCR buffers, nucleotides, DNA polymerase and one or more oligonucleotide primers. Such primers can be designed by procedures well known in the art. Generally, primers should be at least 18 nucleotides in length to minimize the chances of encountering problems with a secondary hybridization site on the vector or insert. Primers with long runs of a single base should generally be avoided. It is generally important to avoid 4 or more G's or C's in a row. For cycle sequencing, primers with melting temperatures in the range 52-58° C., as determined by the (A+T)2+(C+G)4 method, generally produce better results than primers with lower melting temperatures. Primers with melting temperatures above 65° C. should also be avoided because of the potential for secondary annealing. If the template is a high "G-C" template, then a primer with a $T_m$ in the 60-70° C. range may be desirable. It is then advisable to do the sequencing reaction with annealing and extension at 60° C. Primers generally have a G/C content between 40 and 60 percent. For primers with a G/C content of less than 50%, it may be necessary to extend the primer sequence beyond 18 bases to keep the melting temperature above the recommended lower limit of 50° C. It may be desirable for primers to be "stickier" on their 5' ends than on their 3' ends. A "sticky" 3' end as indicated by a high G/C content could potentially anneal at multiple sites on the template DNA. A "G" or "C" may be desirable at the 3' end. Primers should not contain complementary (palindromes) within themselves; that is, they should not form hairpins. If this state exists, a primer will fold back on itself and result in an unproductive priming event that decreases the overall signal obtained. Hairpins that form below 50° C. generally are not such a problem. Primers should generally not contain sequences of nucleotides that would allow one primer molecule to anneal to itself or to the other primer used in a PCR reaction (primer dimer formation). If possible, it is generally useful to run a computer search against the vector and insert DNA sequences to verify that the primer and especially the 8-10 bases of its 3' end are unique.

PCR primers such as those depicted as SEQ ID NO:12 and SEQ ID NO:13, may be utilized in the reaction. Reaction products can be sequenced as described above or separated by gel electrophoresis, e.g., size gel electrophoresis, to identify those plants harboring or not harboring the NOR1110 allele.

Various modifications of general DNA sequencing, PCR, and primer extension techniques are possible as detailed in SHORT PROTOCOLS IN MOLECULAR BIOLOGY (Frederick M. Ausubel et al. eds., 4$^{th}$ ed. 2001) and JOSEPH SAMBROOK & DAVID W. RUSSELL, 1-3 MOLECULAR CLONING: A LABORATORY MANUAL (3d ed. 2001), both of which are hereby incorporated by reference in their entirety.

While specific oligonucleotide primer sequences are described herein, it is understood that substantially identical oligonucleotide primer sequences to those described herein will also work to permit detection of the NOR1110 allele. The term "substantially identical" oligonucleotide primer sequences means that a oligonucleotide primer comprises a sequence that has preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference oligonucleotide sequence using standard alignment programs using standard parameters. Additional primers may also be developed by procedures well known by those of ordinary skill in the art.

The single base pair extension assay may be template-directed dye-terminator incorporation and fluorescence polarization detection (FP-TDI). The FP-TDI assay may include the use of PCR to amplify DNA prior to the FP-TDI assay. In the PCR assay, oligonucleotides such as those depicted in SEQ ID NO:12 and SEQ ID NO:13 may be utilized.

Genetic screening may also be carried out by the ligase detection reaction ("LDR"). In a standard LDR reaction, a pair of probes hybridize to a template adjacent to each other. If there is perfect complementarity at the junction, a high fidelity ligase enzyme ligates the probes. One of the LDR probes is labeled with a fluorescent dye to enable the ligation product to be detected. The resulting LDR products can then be separated by (gel or capillary) electrophoresis as a function of their length, or by hybridizing the ligation products to zipcodes on a universal array through complementary zipcodes appended to the end of one of the LDR probes. The level of multiplexing can be increased by using multiple color dyes.

The ligase detection reaction is well known in the art and described generally in WO 90/17239 to Barany et al., Barany et al., "Cloning, Overexpression and Nucleotide Sequence of a Thermostable DNA Ligase-encoding Gene," *Gene*, 109:1-11 (1991), and Barany F., "Genetic Disease Detection and DNA Amplification Using Cloned Thermostable Ligase," *Proc. Natl. Acad. Sci. USA*, 88:189-193 (1991), which are hereby incorporated by reference in their entirety. In accordance with the present invention, the ligase detection reaction can use two sets of complementary oligonucleotides. This is known as the ligase chain reaction which is described in the three immediately preceding references, which are hereby incorporated by reference in their entirety.

The present invention is further directed to an isolated oligonucleotide having a nucleotide sequence selected from SEQ ID NO:12 and SEQ ID NO:13.

In another aspect, the present invention is directed to a kit for the detection of the NOR1110 allele in a plant. The kit may include an oligonucleotide such as SEQ ID NO:6 or SEQ ID NO:7. The kit may further include materials to perform PCR reactions. The kit may further include one or more buffers. The kit may also include directions for using the kit.

Another aspect of the present invention is directed to a method of genetic screening. This method involves identifying a nucleotide sequence linked to a NOR gene, where the NOR gene comprises a nucleic acid molecule encoding the amino acid sequence of SEQ ID NO:4 and utilizing the nucleotide sequence as a marker to screen or map the NOR gene.

The present invention may be further illustrated by reference to the following examples.

EXAMPLES

The Examples set forth below are for illustrative purposes only and are not intended to limit, in any way, the scope of the present invention.

Example 1

Identification of dfd Allele of NOR

An F2 mapping population was constructed by crossing dfd with the wild tomato species *S. pimpinellifolium* and backcrossing the progeny (F1) with dfd. Fifty five of the F2 plants were genotyped for 104 genetic markers across the tomato genome and phenotype was scored for three traits: color, "extent of wrinkling" (the degree to which the fruit surface appeared wrinkled by visual inspection, scored in arbitrary units), and rate of water loss after harvest. The mapping results showed a high LOD score peak at the north arm of chromosome 10 (between markers TG303 and 5g06430) for the traits of color (LOD score >3) and "extend of wrinkling" (LOD score >3), as shown in FIG. 1.

The NOR gene, which plays a critical role in tomato fruit ripening (Giovannoni, "Genetic Regulation of Fruit Development and Ripening," *Plant Cell* 16:S170-S180 (2004), which is hereby incorporated by reference in its entirety), was mapped to the same approximate location on chromosome 10 (Nor1110 in FIG. 1). This gene represents a candidate gene for conferring the dfd trait. An analysis of the genomic DNA sequences of the NOR alleles from dfd and three normally ripening tomato cultivars (Ailsa Craig, M82, Rutgers) revealed that only one base pair in the coding DNA sequence was different between the dfd allele of NOR and the other cultivars' alleles (t→a at position 1110 of SEQ ID NO:3 and position 483 of SEQ ID NO:2). This base pair substitution is predicted to cause a valine (Val) to aspartic acid (Asp) substitution at position 106 in the polypeptide of SEQ ID NO:1, resulting in the polypeptide of SEQ ID NO:4, and is referred to as the NOR1110 allele.

NOR is a member of the NAC transcription factor protein family (U.S. Pat. No. 6,762,347; Olsen et al., "NAC Transcription Factors: Structurally Distinct, Functionally Diverse," *Trends. Plant Sci.* 10:79-87 (2005), which are hereby incorporated by reference in their entirety). An alignment of amino acid sequences of different members of this family show the Val 106 residue to be highly conserved and a structural prediction locates it in the DNA binding cleft of the transcription factor (Ernst et al., "Structure of the Conserved Domain of ANAC, a Member of the NAC Family of Transcription Factors," *EMBO Rep.* 5:297-303 (2004), which is hereby incorporated by reference in its entirety). According to this structural model, a Val to Asp substitution might have a dramatic effect on the hydrophobic nature of the cleft. These findings suggest that the NOR1110 allelic variant can be used as a marker to track the dfd phenotype.

The mutation in the NOR1110 allele of dfd (t→a at position 1110 of SEQ ID NO:3) is a single nucleotide polymorphism that can be detected using any number of standard molecular biology methods that include isolation of genomic DNA and subsequent mismatch detection method or direct sequencing to determine DNA sequence or to infer one of two allelic species as defined by the presence or absence of the NOR1110 SNP.

Figure 2:
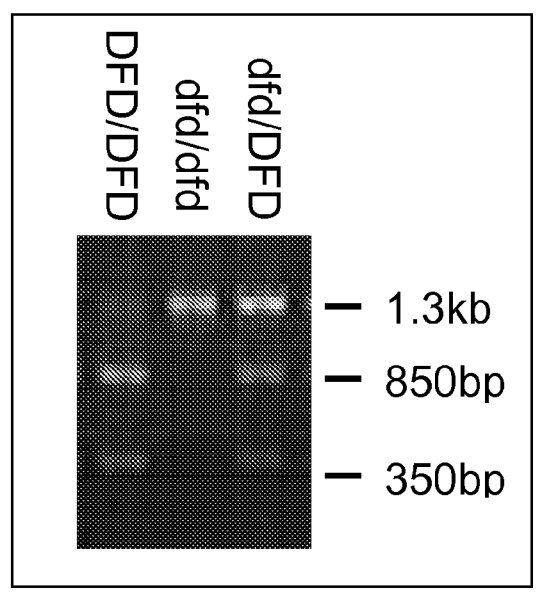
FIG. 2 is a photograph of agarose gel electrophoresis of the PCR products resulting from the reactions of Nor-F (SEQ ID NO:12) and Nor1556 (SEQ ID NO:13) primers with genomic DNA from the dfd mutant (dfd/dfd), normally softening tomato cultivar Ailsa Craig (DFD/DFD), and an F1 heterozygote of dfd x Ailsa Craig (dfd/DFD).

Specifically, the mutation in the NOR1110 allele of dfd abolishes a digestion site by the BsrFI restriction enzyme (gccggt→gccgga). Based on this polymorphism, the genotyping assay CAPS (cleaved amplified polymorphic sequence) marker was developed with the primers:

```
                                  (SEQ ID NO: 12)
Nor-F 5'-ACTCATCGTCCACTACCTCA-3'
and (SEQ ID NO: 13)
Nor1556 5'-TGTCGAACCTCTTTCGGCTA-3'
``` to give a PCR product of 1,307 bp. Digestion with BsrFI of the product of the PCR reaction using these PCR primers with normally ripening tomato (e.g., Ailsa Craig, Rutgers and M82) genomic DNA as a template, yields two DNA fragments of 860 and 447 bp (FIG. 2). This product is referred to as marker Nor1110.

As noted above, the F2 mapping population (dfd x *S. pimpinellifolium*) was genotyped for the Nor1110 marker and it was mapped to chromosome 10, between the markers 5g06430 and TG303, coinciding with a high LOD score peak found for the color and the "extent of wrinkling" traits (FIG. 1). To evaluate the frequency of Nor1110 in other tomato lines, the Nor1110 marker was used to screen genomic DNA from 60 tomato cultivars. None of the 60 lines carried Nor1110. However, in a second screen, Nor1110 was present in the alc mutant, as well as 37 long shelf tomato lines from Spain.

For this second screen, all tomato (*Solanum lycopersicum*) plants (Ailsa Craig, dfd, wild tomato species *Solanum pimpinellifolium* (accession LA1589), and the progeny of their crosses) were grown in the green house as described in Saladie et al, "A Re-evaluation of the Key Factors That Contribute to Tomato Fruit Softening and Integrity," *Plant Physiology* 144:1012-1028 (2007), which is hereby incorporated by reference in its entirety, except for a collection of unnamed long shelf life tomato cultivars from Spain which were grown in the field (Freeville, N.Y.; summer 2006) under standard conditions.

An F2 mapping population was constructed by crossing dfd with the wild tomato species *S. pimpinellifolium* (accession LA1589) and backcrossing the progeny (F1) with dfd. Genomic DNA was extracted according to Fulton et al., "Microprep Protocol for Extraction of DNA from Tomato and Other Herbaceous Plants," *Plant Mol. Biol. Rep.* 13:207-209 (1995), which is hereby incorporated by reference in its entirety, and subjected to marker analysis of 104 genetic markers across the tomato genome, according to the consensus map Tomato-EXPIMP 2001 (available through the Solanaceae Genomics Network website; www.sgn.cornell.edu). Fruits were phenotyped for three traits: color (yellow, orange, pink, or red), "extent of wrinkling" (the degree to which the fruit surface appeared wrinkled by visual inspection, scored in arbitrary units 1-5), and rate of water loss after harvest. Genotype and phenotype data were analyzed using QGENE software (Nelson, "QGENE: Software for Marker-based Genomic Analysis and Breeding," *Molecular Breeding* 3:239-245 (1997), which is hereby incorporated by reference in its entirety.

For the CAPS (cleaved amplified polymorphic sequence) marker Nor1110, genomic DNA was extracted and amplified by PCR, using the primers:

```
Nor-F 5'-ACTCATCGTCCACTACCTCA-3'
and

Nor1556 5'-TGTCGAACCTCTTTCGGCTA-3'
``` to give a PCR product of 1,307 bp. Digestion with BsrFI of the product of the PCR reaction followed and products were analyzed by agarose gel (1%) electrophoresis.

What is claimed:

1. A vector comprising a nucleic acid molecule comprising a NOR gene having the NOR1110 allele of dfd, wherein the NOR gene is operatively linked to a heterologous promoter.

2. The vector according to claim 1, wherein the promoter is capable of expression within a plant cell.

3. A transgenic tomato plant with reduced or delayed softening and deterioration of fruit compared to its respective wild-type plant, said transgenic tomato plant comprising the vector according to claim 2.

4. A method of imparting to a tomato plant a dfd trait, said method comprising:

transforming a tomato plant with the vector according to claim 2 and expressing the vector in the tomato plant, whereby expression of the vector causes expression of the NOR gene having the NOR1110 allele of dfd, thereby imparting to the tomato plant the dfd trait.

5. The vector according to claim 1, wherein the NOR gene having the NOR1110 allele of dfd encodes a protein having the amino acid sequence of SEQ ID NO:4.

6. The method according to claim 4, wherein the NOR gene having the NOR1110 allele of dfd encodes a protein having the amino acid sequence of SEQ ID NO:4.

* * * * *